United States Patent [19]

Purdy et al.

[11] Patent Number: 5,085,648
[45] Date of Patent: Feb. 4, 1992

[54] DUAL DIAMETER NEEDLE WITH A SMOOTH TRANSITION

[75] Inventors: Edmund R. Purdy, Fruit Height; Gerald H. Peterson, Salt Lake City; Timothy J. Erskine, both of Salt Lake City, all of Utah

[73] Assignee: Becton Dickinson and Company, Franklin Lakes, N.J.

[21] Appl. No.: 582,262

[22] Filed: Sep. 13, 1990

[51] Int. Cl.$^5$ .............................. A61M 5/32
[52] U.S. Cl. ........................ 604/198; 604/272
[58] Field of Search ............... 604/192, 198, 239, 263, 604/264, 272-274

[56] References Cited

U.S. PATENT DOCUMENTS

| | | | |
|---|---|---|---|
| 824,686 | 6/1906 | Daniel | 604/274 |
| 2,828,744 | 4/1958 | Hirsch et al. | 604/272 |
| 2,899,960 | 8/1959 | Ginsburg | 604/272 |
| 3,386,438 | 6/1968 | Stevens | 604/272 |
| 3,831,814 | 8/1974 | Butler | 604/274 |
| 4,617,019 | 10/1986 | Fecht et al. | 604/274 |
| 4,735,611 | 4/1988 | Anderson et al. | 604/272 |
| 4,735,612 | 4/1988 | Chevalier | 604/272 |
| 4,767,407 | 8/1988 | Foran | 604/239 |
| 4,911,694 | 3/1990 | Dolan | 604/198 |
| 4,929,241 | 5/1990 | Kulli | 604/192 |

FOREIGN PATENT DOCUMENTS 2202446  9/1988  United Kingdom ............... 604/198

Primary Examiner—C. Fred Rosenbaum
Assistant Examiner—Sharon Finkel
Attorney, Agent, or Firm—Aaron Passman

[57] ABSTRACT

A needle cooperates with a tip cover the coaxially fits about the needle and slides axially relative thereto. A thin walled tube of the needle has a shank portion extending from the proximal end toward the distal end and a tip portion extending from the distal end toward the proximal end. The tip portion has a diameter that is larger than the diameter of the shank portion. The needle includes a transition zone between the shank and tip portions wherein the axial distance of the transition zone is about an order of magnitude greater than the difference in the diameters of the tip and shank portions. The tip portion includes a bevel extending from the distal end toward the transition zone as a sharpened edge to ease insertion. The cover includes a bearing and a tip protecting part. The bearing is sized to coaxially fit about the shank portion and slide axially relative thereto. The difference in the diameters of the tip and shank portions is such that the bearing can not slide distally over the transition zone. The cover is positioned on the needle to locate the tip protecting part over the sharpened edge when the bearing is at the transition zone. The transition zone is shaped frusto conically and is located between the shank and tip portions. The frusto conical shape is at angle relative to the axis of the needle due to a difference in the first and second diameters thus providing a diametrical imperceptible change.

2 Claims, 1 Drawing Sheet

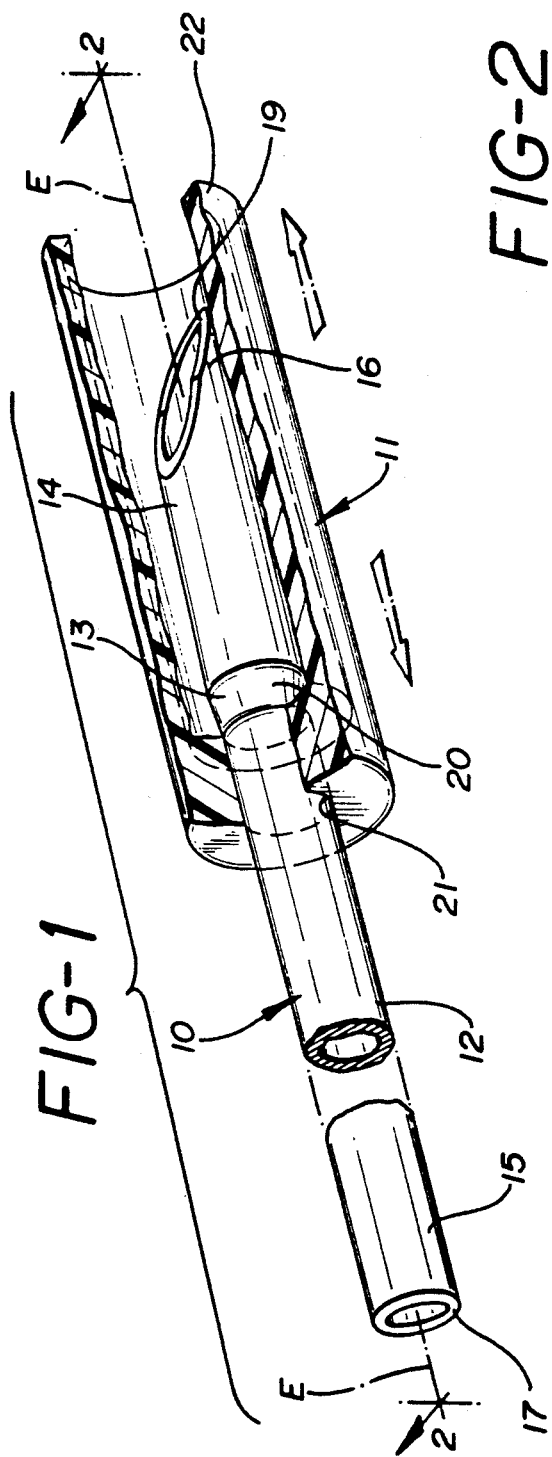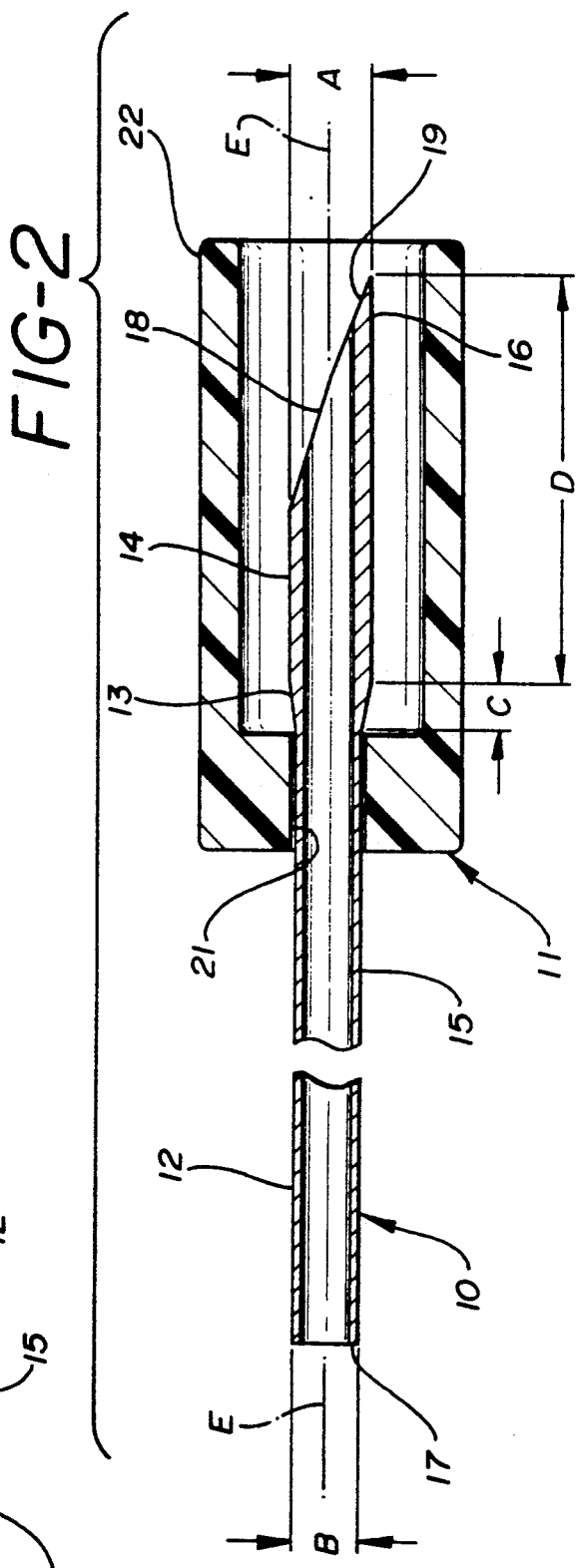

DUAL DIAMETER NEEDLE WITH A SMOOTH TRANSITION

FIELD OF THE INVENTION

A needle for intravenous use with a needle tip cover that coaxially fits about the needle and slides axially relative thereto, and more particularly the needle has different diameters with an imperceptible change therebetween.

BACKGROUND

With concern about infection, transmission of AIDS, hepatitis and similar incurable diseases of the blood, methods and devices to enclose the used disposable needle tip have become very important and in great demand. Many approaches to guard the needle, protect users and/or otherwise prevent injury have been proposed. All of them are cumbersome, expensive and interfere with the normal and accepted procedure for the insertion of an over the needle catheter. Typical of such introducers is U.S. Pat. No. 4,846,805 wherein the shield slides over the flash chamber body to engage the catheter and lock about the used needle tip.

Specifically, after the catheter has been inserted by an over the needle procedure and blood flashback has been observed, the catheter is advanced and/or the needle is withdrawn. After the catheter is inserted into the vessel as desired and the needle is withdrawn and discarded, protection of the used needle tip is important. Cumbersome needle guards interfere with the single hand over the needle catheter placement procedure. The needle tip cover disclosed herein does not interfere with or require any additional mechanisms which interfere with the accepted over the needle technique.

U.S. Pat. No. 4,139,009 has a needle tip protector with a permanently attached cover surrounding the needle and a number of elastic arms which extend along the length of the needle. The arms are constructed so as to bow outwardly from the needle shank when the needle is pressed against and into the patient. U.S. Pat. No. 4,660,570 shows a needle tip protector with a membrane extending over the sharp point of the needle whereby penetration causes the needle to extend through the membrane and the skin of the patient.

U.S. Pat. No. 4,650,468 has a device with a sleeve concentrically placed about the needle shank. A safety shield at one end has a rubber membrane extending across an opening in the shield. The membrane is adapted to be pierced by the needle tip for use.

U.S. Pat. No. 2,828,744 discloses a flexible needle assembled from an enlarged metal end and a resilient tube. The metal end and the resilient tube have different diameters. The idea behind this patent is to provide a flexible tube that can be left in the blood vessel and the two piece assembly is for that purpose. U.S. Pat. No. 4,250,881 discloses a needle having an end that is spread so as to prevent the catheter coaxially placed on the needle proximal of the end from experiencing compressive loads during insertion. The catheter is soft and the idea is to prevent the bunching or accordion like folding of the catheter due to the penetration of the tissue.

There is no teaching or disclosure of anything which provides the diameter change with a particular geometry found to retain a needle tip cover from removal over the needle tip and yet with a needle which has such a small change in shape that there appears to be no perceptible shape change. The idea of having to be the recipient of an enlarged needle tip during a catheter insertion or the like is offensive to most people. The problem of changing the diameter imperceptably is resolved herein.

SUMMARY OF THE INVENTION

The preferred invention is a needle which cooperates with a needle tip cover that coaxially fits about the needle and slides axially relative thereto. The needle is for intravenous use and has a thin walled tube with a distal end and a proximal end. A shank portion of the thin walled tube extends from the proximal end toward the distal end and a tip portion of the thin walled tube extends from the distal end toward the proximal end. The tip portion has a diameter that is larger than the diameter of the shank portion. The preferred needle includes a transition zone between the shank and tip portions wherein the axial distance of the transition zone is about an order of magnitude greater than the difference in the diameters of the tip and shank portions.

The tip portion is most preferably shorter in axial length than the shank portion and the axial length of the lltransition zone is shorter than the axial length of the tip portion. The tip portion may include a bevel extending from the distal end toward the transition zone for providing a sharpened edge to ease insertion into a vessel. The transition zone may have a generally frusto conical shape.

A needle and cooperative needle tip cover are also a part of the preferred invention. The cover may include a bearing and a tip protecting part. The bearing is most preferably sized to coaxially fit about the shank portion and to slide axially relative thereto. The difference in the diameters of the tip and shank portions is such that the bearing can not slide distally over the transition zone. The cover is preferably positioned on the needle to locate the tip protecting part over the sharpened edge when the bearing is at the transition zone thus preventing the removal of the cover from the needle by axial movement toward the distal end. The transition zone is most preferably shaped frusto conically and is located between the shank and tip portions. The frusto-conical shape is at an angle relative to the axis of the needle due to the difference in the first and second diameters thus providing an imperceptible diameter change. The preferred angle is in a range of about 2 to 8 degrees relative to the axis of the needle due to the difference in the diameters of the tip and shank portions.

BRIEF DESCRIPTION OF THE DRAWINGS

FIG. 1 is a perspective view of a needle and tip cover of the preferred embodiment and the tip cover is shown partially in section on the shank portion proximal of the transition zone between the shank and tip portions of the needle.

FIG. 2 is a view of the needle and tip cover of FIG. 1 shown in a cross section taken along line 2—2 of FIG. 1.

DETAILED DESCRIPTION OF THE DRAWINGS

While this invention is satisfied by embodiments in many different forms, there is shown in the drawings and will herein be described in detail, a preferred embodiment and alternate embodiments of the invention, with the understanding that the present disclosure is to be considered as exemplary of the principles of the invention and is not intended to limit the invention to any one of the embodiments illustrated. The scope of the invention will be measured by the appended claims and their equivalents.

FIG. 1 is a perspective view of a needle 10 and a tip cover 11 of the preferred embodiment and the tip cover 11 is shown partially in section on a shank portion 12 proximal of a transition zone 13 between the shank portion 12 and a tip portion 14 of the needle 10. The needle 10 cooperates with the needle tip cover 11 that coaxially fits about the needle 10 and slides axially relative thereto. The needle 10 is for intravenous use and is made of a thin walled metallic tube 15 with a distal end 16 and a proximal end 17. The shank portion 12 of the thin walled tube 15 extends from the proximal end 17 toward the distal end 16. The tip portion 14 of the thin walled tube 15 extends from the distal end 16 toward the proximal end 17.

The tip portion 14 has a diameter "A" that is larger than the diameter "B" of the shank portion so that the transition zone 13 results between the shank and tip portions 12 and 14. The axial distance of the transition zone 13 is about an order of magnitude greater than the difference in the diameters (A minus B) of the tip and shank portions 12 and 14.

FIG. 2 is a view of the needle 10 and tip cover 11 of FIG. 1 shown in a cross section taken along line 2—2 of FIG. 1. The tip portion 14 is shorter in axial length "D" than the shank portion 12 and the axial length "C" of the transition zone 13 is shorter than the axial length "D" of the tip portion 14. The tip portion 14 includes a bevel 18 extending from the distal end 16 toward the transition zone 13 for providing a sharpened edge 19 to ease insertion into a blood vessel (not shown). The transition zone 13 has a generally frusto-conical shape 20. The surface of the frusto conical shape 20 is at angle relative to an axis "E" of the needle 10 due to a difference in the first and second diameters "A and B" for providing an imperceptible change in diameter "A minus B".

The difference in diameters "A and B" between the tip portion 14 and the shank portion 12 in a preferred embodiment is approximately in the range of 0.0762 to 0.127 mm. The axial length "C" of the transition zone 13 is approximately in the range of 0.38 to 1.14 mm. The frusto conical shape 20 is located between the shank and tip portions 12 and 14 and the surface of the frusto-conical shape 20 is at in the range of angle of about 2 to 8 degrees relative to the axis "E" of the needle due to the difference in the diameters of the tip and shank portions 14 and 12.

The cover 11 cooperates with the needle 10 and includes a bearing 21 and a tip protecting part 22. The bearing 21 is sized to coaxially fit about the shank portion 12 and slide axially relative thereto. The bearing 21 can not slide distally along the needle 10 over the transition zone 13. The cover 11 is positioned on the needle 10 so as to locate the tip protecting part 22 over the sharpened edge 19 when the bearing 21 is distally located at the transition zone 13 and preventing the removal of the cover 11 from the needle 10 by further axial movement toward the distal end 16. The needle 10 is preferably made of a medical grade stainless steel and the cover 11 is composed of a polymer. The needle 10 can be made with two diameters and the transition zone 13 therebetween by machining, etching, drawing or other process which changes a one diameter tube. The cover 11 can be molded or cast.

The preferred needle 10 as disclosed herein has an impercentible change in diameter "A minus B". Casual examination of the needle 10 without the assistance of instruments, optical magnifying equipment or measuring devices would not suggest to the observer that the needle 10 has two diameters "A and B". Unless the observation were made with knowledge that there was the tip portion 14 of the needle 10 with a larger diameter, there would be no notice of a change in diameter from "A to B". Especially for intravenous use, needles should appear smooth and of a minimum diameter so that the patient does not fear pain. As used herein the term imperceptible means, that with ordinary observation unaided by prior knowledge or the aforesaid instruments, equipment or devices, the needle appears smooth and of substantially constant diameter.

What is claimed is:
1. A needle and cooperative needle tip cover comprising:
    a needle including thin walled tube with a distal end and a proximal end;
    a shank portion of the thin walled tube extending from the proximal end toward the distal end;
    a tip portion of the thin walled tube extending from the distal end toward the proximal end, the tip portion of a diameter that is larger than the diameter of the shank portion;
    a cover including a bearing and a tip protecting part, the bearing sized to coaxially fit about the shank portion and slide axially relative thereto;
    a transition zone between the shank and tip portions wherein the axial distance of the transition zone is about an order of magnitude greater than the difference in the diameters of the tip and shank portions and the bearing can not slide distally along the needle over the transition zone.
2. The needle and cover of claim 1 wherein the cover is positioned on the needle to locate the tip protecting part over the sharpened edge when the bearing is at the transition zone and to prevent the removal of the cover from the needle by axial movement toward the distal end.

* * * * *